(12) United States Patent
Westrum et al.

(10) Patent No.: US 8,486,345 B1
(45) Date of Patent: Jul. 16, 2013

(54) MOBILE SANITIZER UNIT

(76) Inventors: Corey S. Westrum, Leonard, MN (US); Susan A. Westrum, Leonard, MN (US); Jason D. Vant Hul, Bagley, MN (US)

( * ) Notice: Subject to any disclaimer, the term of this patent is extended or adjusted under 35 U.S.C. 154(b) by 682 days.

(21) Appl. No.: 12/605,003

(22) Filed: Oct. 23, 2009

(51) Int. Cl.
*A61L 2/04* (2006.01)

(52) U.S. Cl.
USPC .......................................... 422/307; 422/292

(58) Field of Classification Search
USPC .................................................. 422/292, 307
See application file for complete search history.

(56) References Cited

U.S. PATENT DOCUMENTS

| | | | |
|---|---|---|---|
| 2,096,838 A | 10/1937 | Baker | |
| 3,222,948 A * | 12/1965 | DeMart | 74/89.28 |
| 4,961,283 A | 10/1990 | Forbes | |
| 5,282,322 A | 2/1994 | Kasuya | |
| 6,117,687 A * | 9/2000 | Hugh | 436/183 |
| 6,141,901 A | 11/2000 | Johnson et al. | |
| 6,612,067 B2 | 9/2003 | Topp | |
| 2003/0026727 A1 | 2/2003 | Topp | |
| 2004/0028554 A1 | 2/2004 | Hedman | |
| 2005/0127069 A1 | 6/2005 | Zapf et al. | |
| 2005/0246942 A1 | 11/2005 | Mueller et al. | |
| 2007/0062063 A1 | 3/2007 | Langley | |

* cited by examiner

*Primary Examiner* — Sean E Conley
(74) *Attorney, Agent, or Firm* — Neustel Law Offices

(57) ABSTRACT

A mobile sanitizer unit for thoroughly sanitizing objects through the use of evenly distributed heat in a mobile trailer. The mobile sanitizer unit generally includes an enclosed chamber positioned upon a trailer vehicle frame for sanitizing objects (e.g. furniture, mattresses, fabric, etc.) within. The chamber includes a heater with that is separated from the contained objects to prevent overheating a specific area of the objects. The heat is circulated via one or more circulation fans. A floor passageway may also be defined for circulating the heated air underneath the objects. A plurality of temperature sensors are used to record the internal core temperature of the objects along with the ambient temperature within the chamber. A separately accessible control room may also be located upon the vehicle frame and include a controller therein for receiving data from the temperature sensors and for controlling the heater and the circulation fans.

15 Claims, 6 Drawing Sheets

MOBILE SANITIZER UNIT

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a sanitizer unit and more specifically it relates to a mobile sanitizer unit for thoroughly sanitizing objects through the use of evenly distributed heat in a mobile trailer.

2. Description of the Related Art

Any discussion of the related art throughout the specification should in no way be considered as an admission that such related art is widely known or forms part of common general knowledge in the field.

Bed bugs and other insects are commonly known to exist in various objects, including furniture, beds, fabrics, etc. One method sanitizing the objects is to coat the objects with various sanitizing chemicals. Because of the potentially dangerous health and environmental effects of the chemicals, the use of the chemicals is often times not recommended or desired. Another method of sanitizing the objects is to apply heat to the object. However, the prior art has not shown a device that evenly distributes the heat throughout the object both externally and internally. Because of the inherent problems with the related art, there is a need for a new and improved mobile sanitizer unit for thoroughly sanitizing objects through the use of evenly distributed heat in a mobile trailer.

BRIEF SUMMARY OF THE INVENTION

A system for thoroughly sanitizing objects through the use of evenly distributed heat in a mobile trailer. The invention generally relates to a sanitizer unit which includes an enclosed chamber positioned upon a trailer vehicle frame for sanitizing objects (e.g. furniture, mattresses, fabric, etc.) within. The chamber includes a heater with that is separated from the contained objects to prevent overheating a specific area of the objects. The heat is circulated via one or more circulation fans. A floor passageway may also be defined for circulating the heated air underneath the objects. A plurality of temperature sensors are used to record the internal core temperature of the objects along with the ambient temperature within the chamber. A separately accessible control room may also be located upon the vehicle frame and include a controller therein for receiving data from the temperature sensors and for controlling the heater and the circulation fans.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview.

Figure 1:
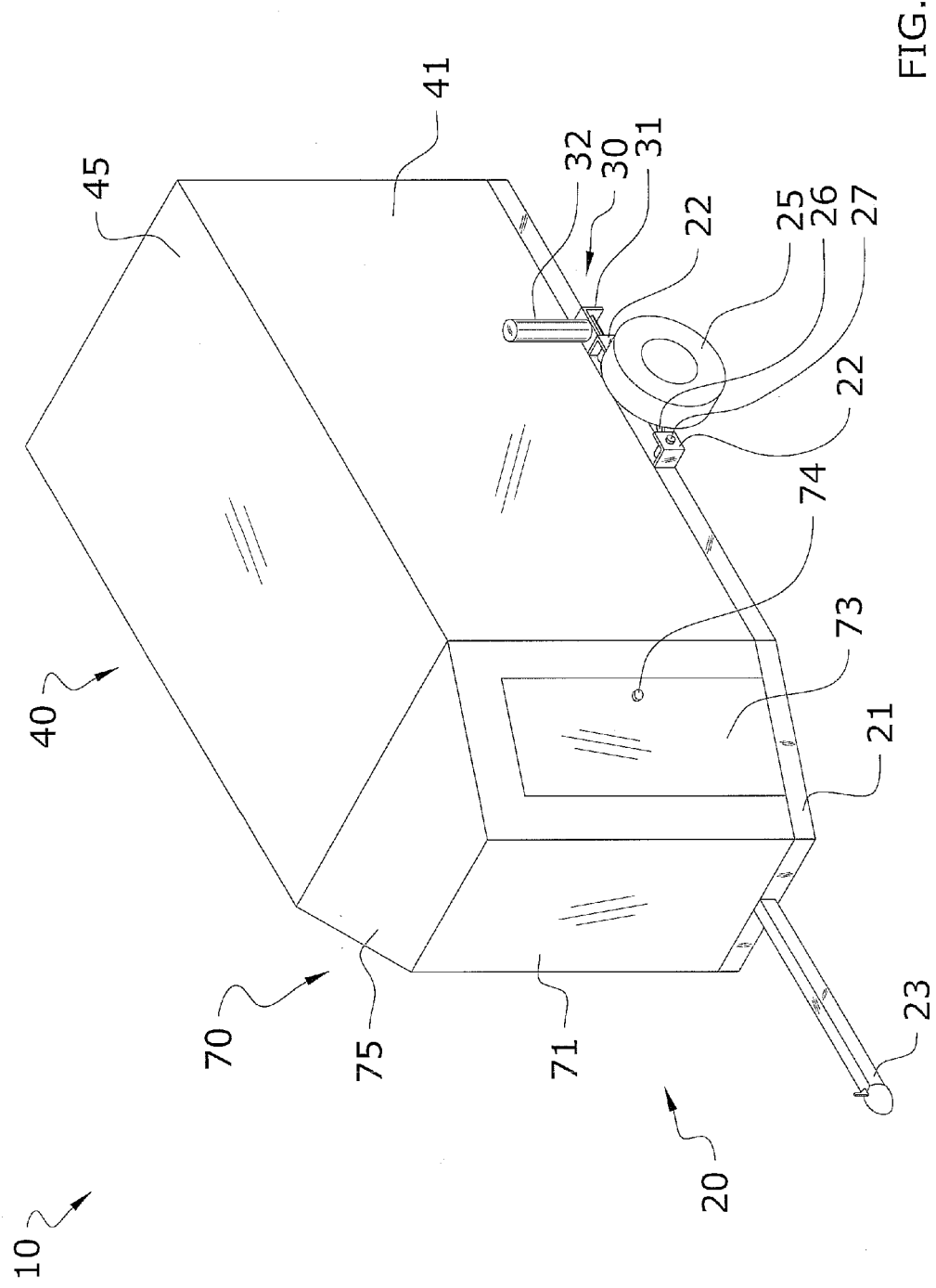
FIG. 1 is an upper perspective view of the present invention.
Figure 2:
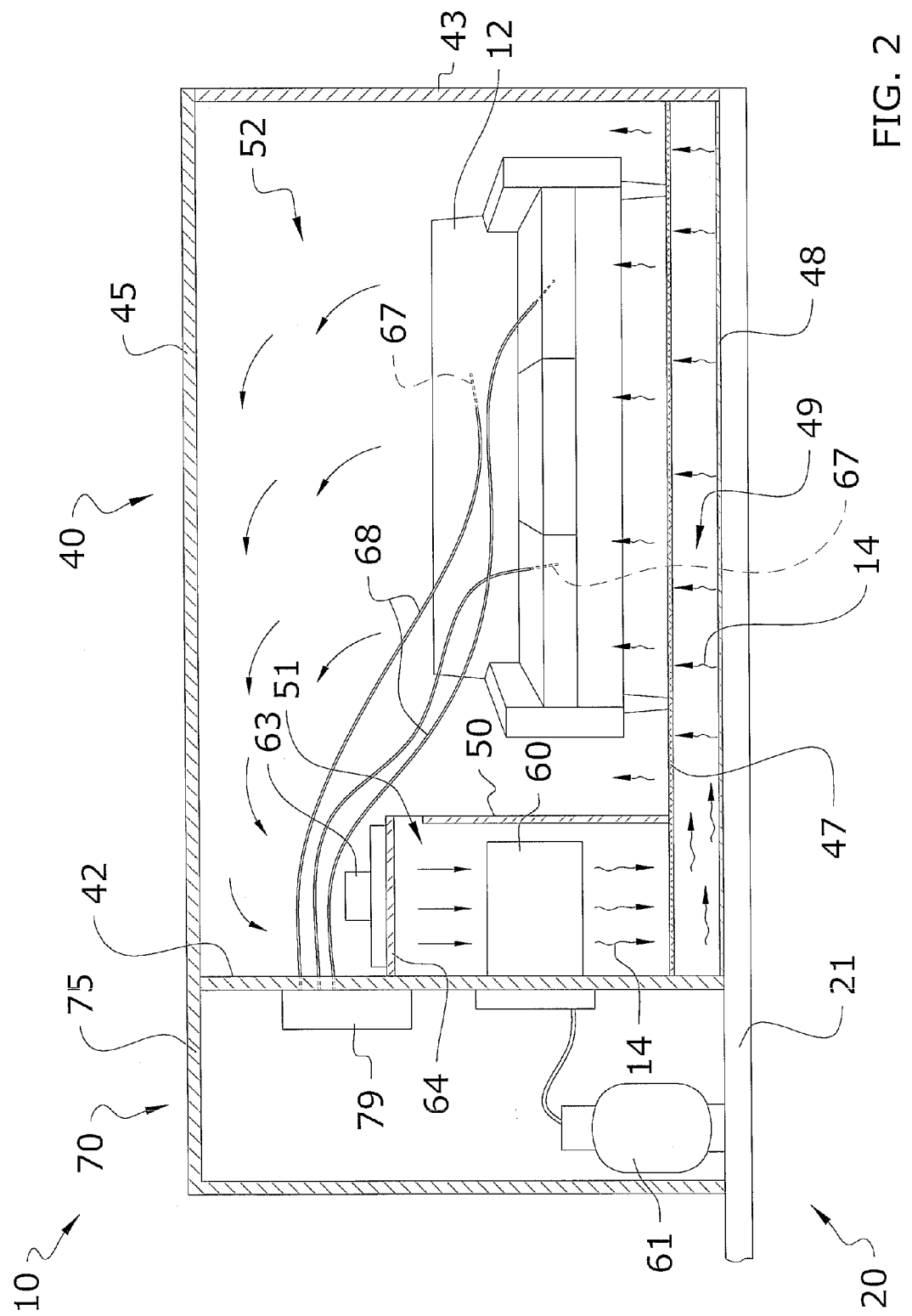
FIG. 2 is a side-sectional view of the present invention in use.
Figure 3:
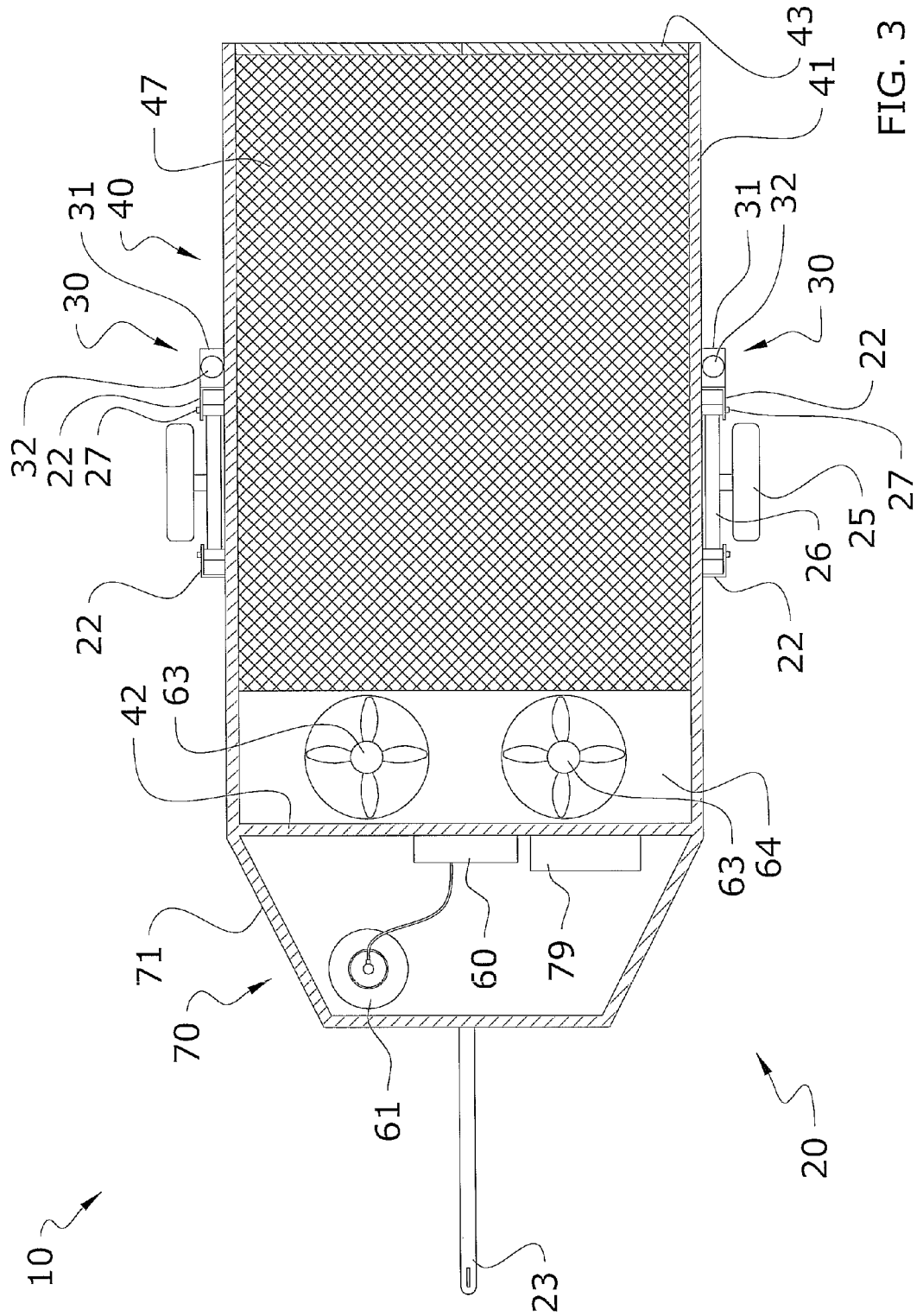
FIG. 3 is a top-sectional view of the present invention.
Figure 4:
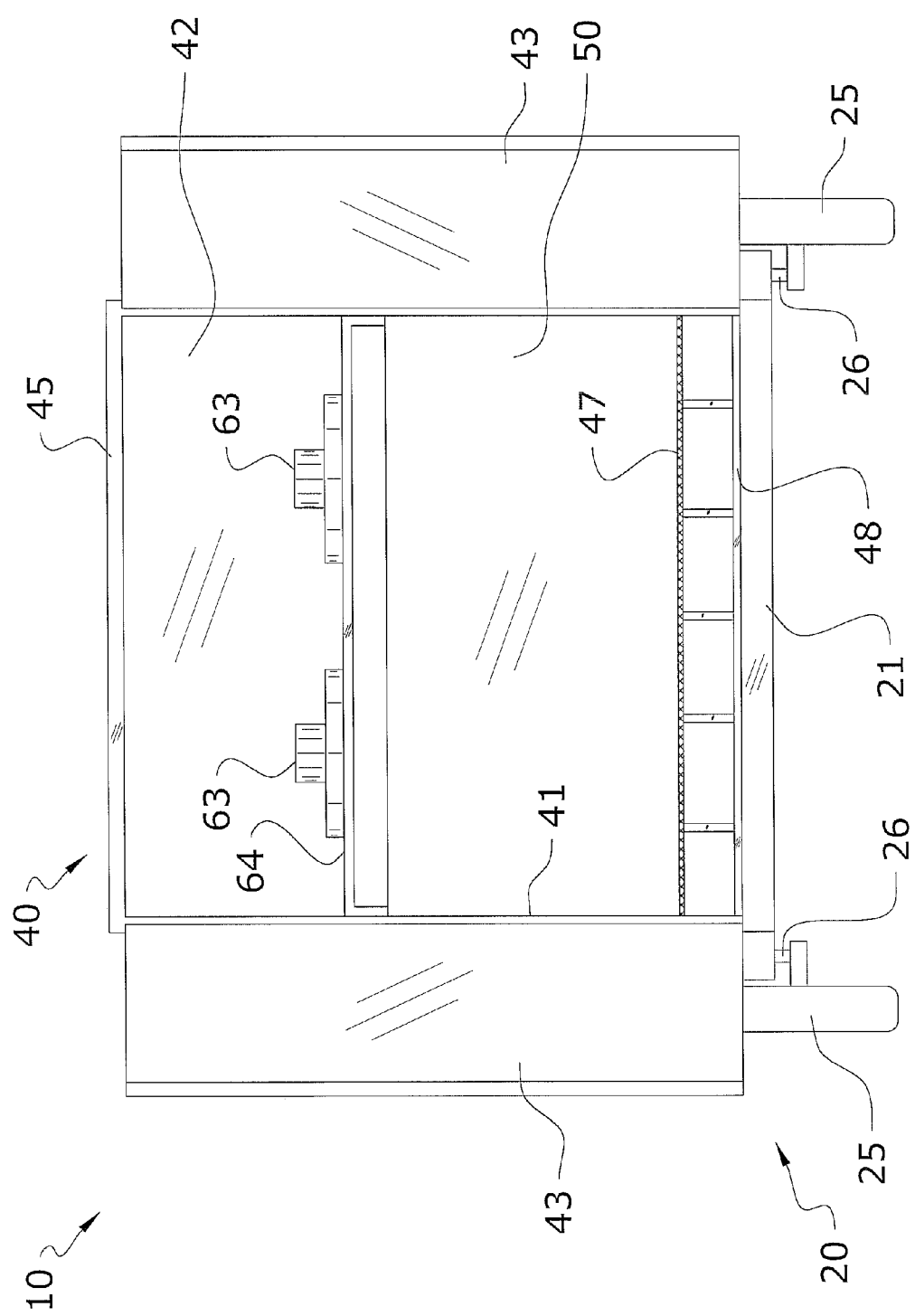
FIG. 4 is a rear view of the present invention viewing within the chamber.
Figure 5:
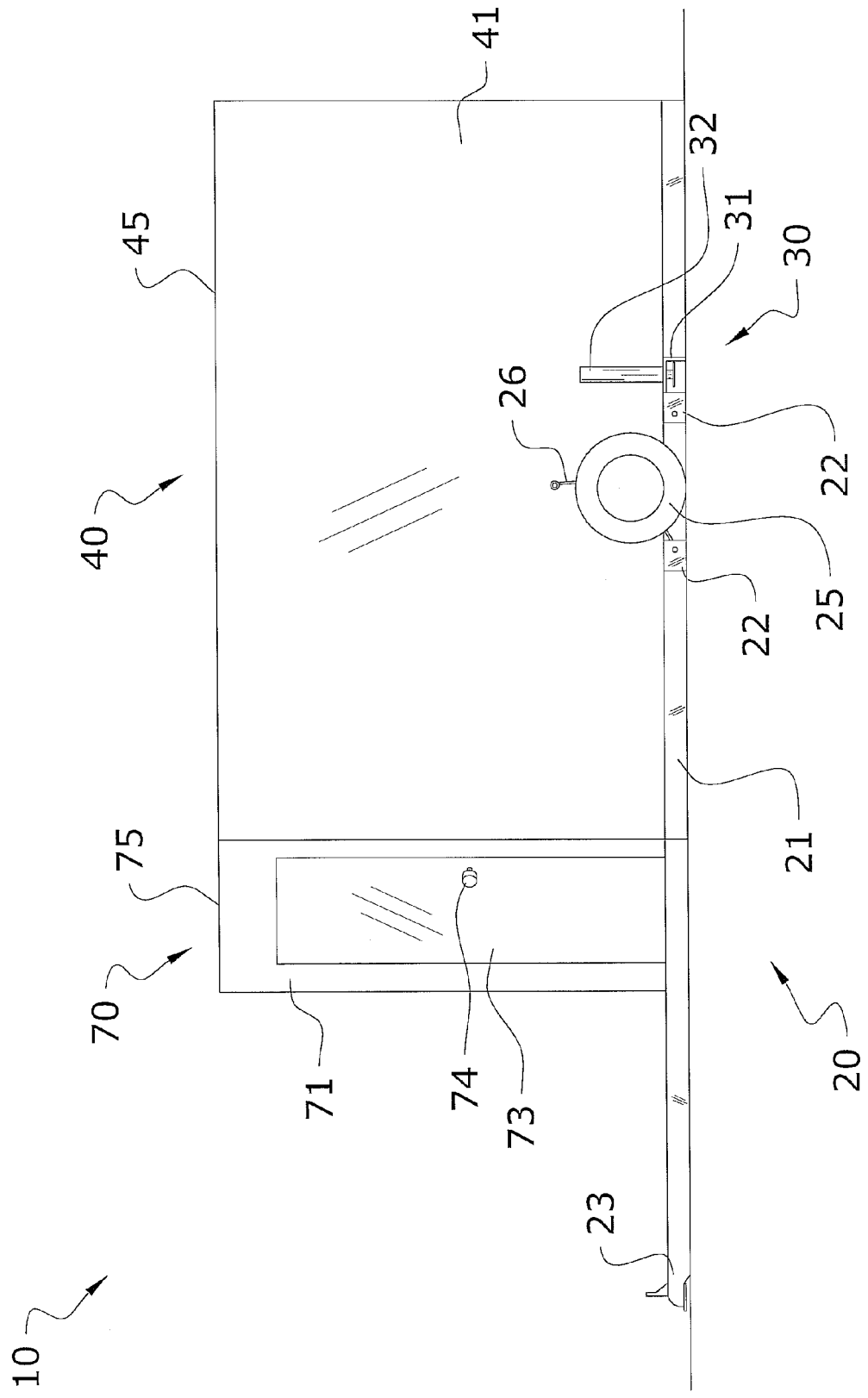
FIG. 5 is a side view of the present invention in a lowered position.
Figure 6:
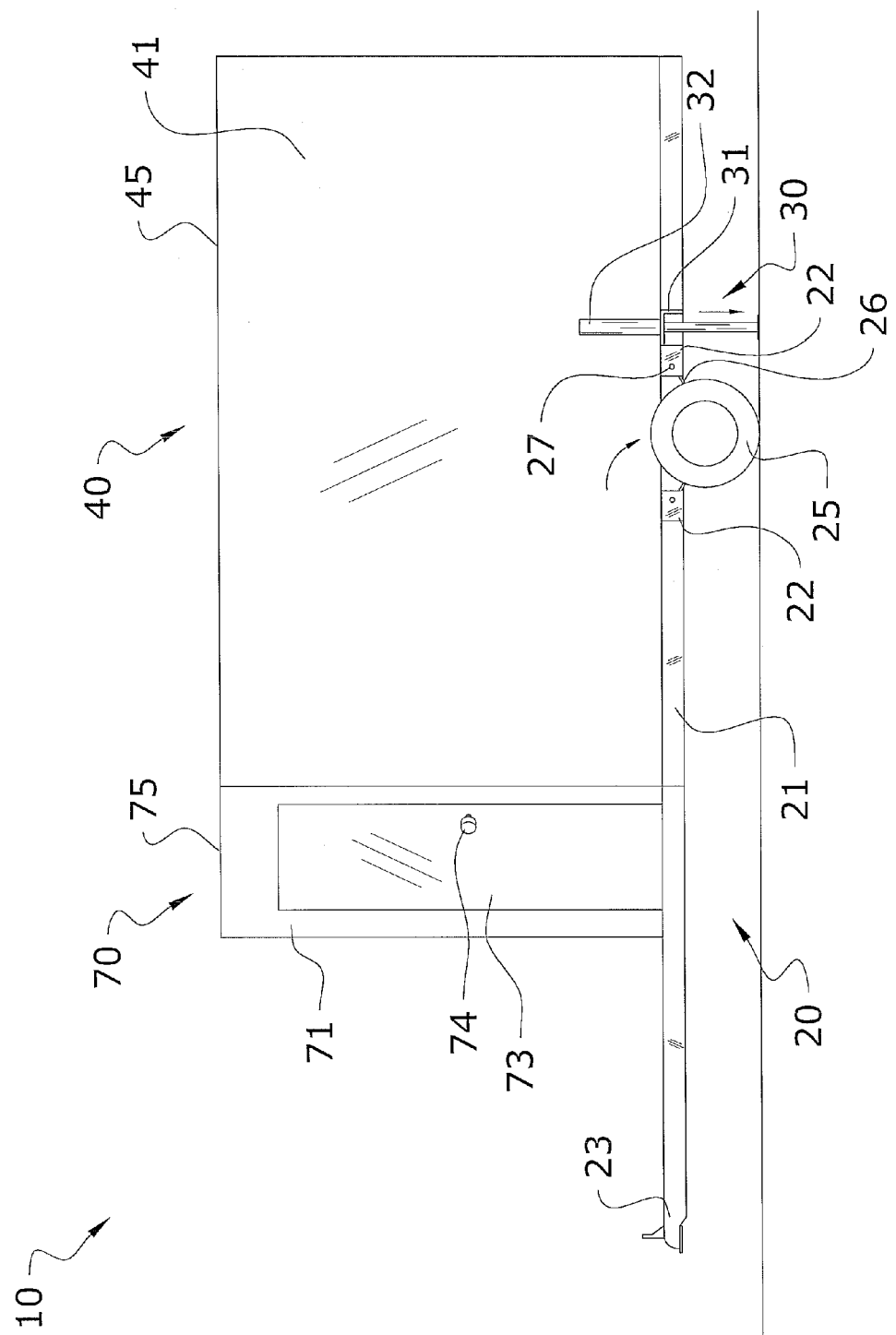
FIG. 6 is a side view of the present invention in a raised position.

Turning now descriptively to the drawings, in which similar reference characters denote similar elements throughout the several views, FIGS. 1 through 6 illustrate a mobile sanitizer unit 10, which comprises an enclosed chamber 40 positioned upon a trailer vehicle frame 21 for sanitizing objects 12 (e.g. furniture, mattresses, fabric, etc.) within. The chamber 40 includes a heater 60 with that is separated from the contained objects 12 to prevent overheating a specific area of the objects 12. The heated air 14 is circulated via one or more circulation fans 63. A floor passageway 49 may also be defined for circulating the heated air 14 underneath the objects 12. A plurality of temperature sensors 67 are used to record the internal core temperature of the objects 12 along with the ambient temperature (ambient temperature sensors not shown) within the chamber 40. A separately accessible control room 70 may also be located upon the vehicle frame 21 and include a controller 79 therein for receiving data from the temperature sensors 67 and for controlling the heater 60 and the circulation fans 63. The term "objects" herein may include various structures in which sanitization of such is desirable, such as mattresses, couches, chairs, other furniture, fabrics, carpet, clothing, etc.

B. Vehicle Frame.

The present invention is generally configured in a vehicle 20 embodiment, such as a pull-type trailer. However, it is appreciated that the present invention may be embodied in a drivable vehicle structure or a stationary structure. The vehicle 20 of the preferred embodiment includes a frame 21 forming the base of the present invention to support 64 the chamber 40, control room 70, and various other components of the present invention. A receiver hitch 23 preferably extends from the frame 21 for attaching to a pulling vehicle 20 to pull the frame 21.

The frame 21 also preferably includes one or more sets of wheels 25 and fenders (not shown) partially surrounding the wheels 25 as appreciated. In the illustrated embodiment, detachable leaf springs 26 are used with the wheels 25. The leaf springs 26 provide conventional use and are also able to detach from a mount 22 connected to the frame 21 via the removal of a pin 27 to allow the frame 21 and thus vehicle 20 to be lowered with respect to the wheels 25, wherein the frame 21 is essentially disconnected from the wheels 25 to be movable therefrom.

C. Lift System.

A pair of brackets 31 are preferably secured to the frame 21 along the sides of the frame 21 preferably at a location that will allow for the frame 21 to be balanced while lifting or lowering the frame 21. An actuator 32 is secured to each respective bracket 31 for providing the lowering and lifting force for the vehicle 20. The actuators 32 may be comprised of various types, such as but not limited to electric, hydraulic, or manually crank-operated.

It is appreciated that various other lift systems 30 may be utilized with the vehicle 20 rather than the detachable leaf spring 26 and actuator 32 as described herein all which preferably allow for the vehicle 20 to be lowered to the ground surface for easier loading and to be raised above the ground surface thus allowing the vehicle 20 to be pulled or driven.

D. Chamber.

A chamber 40 is secured to the frame 21 for sanitizing objects 12 therein through the use of heat. The chamber 40 is comprised of an enclosed structure and includes a pair of sidewalls 41, a front wall 42, and a rear wall which is generally comprised of a pair of doors 73 including handles to allow access within the chamber 40. The two doors 73 allow for large objects 12, such as furniture to be loaded within the chamber 40. The walls and floors may be comprised of various materials, such as but not limited to aluminum, wood, or fiberglass. The chamber 40 is generally insulated to retain heat and provide for an overall more efficient heating process, such as with polystryene.

The floor of the chamber 40 is generally comprised of a perforated floor 47 and a sub-floor 48 vertically offset below the perforated floor 47 thus forming a passageway 49 therebetween. The perforated floor 47 and sub-floor 48 preferably extend throughout the bottom of the chamber 40. The perforated floor 47 may be comprised of various structures, such as but not limited to expanded metal. The passageway 49 and perforated floor 47 allows for the heat to be circulated beneath the object 12 within the chamber 40 to more evenly distribute the heated air 14 and thus more evenly heat the object 12.

The chamber 40 also generally includes a partition 50 at least partially separating the chamber 40 into a directly heated space 51 and an indirectly heated space 52. The partition 50 generally extends only partially along a vertical height of the inside of the chamber 40 and preferably near the lower part of the inside of the chamber 40, such as to extend towards the perforated floor 47. The partition 50 does not extend below the perforated floor 47, wherein the circulated heat is able to travel between the directly heated space 51 and an indirectly heated space 52 both above the partition 50 and within the passageway 49 below the partition 50.

The indirectly heated space 52 is generally larger than the directly heated space 51, wherein the indirectly heated space 52 is directly accessible via the doors 73 of the chamber 40 and is used for positioning the objects 12 therein. The second chamber 40 is used for positioning the heater 60 within. The heater 60 is separated from the objects 12 via the partition 50 to prevent overheating of the objects 12 in a certain spot of the objects 12 and to allow a more even distribution of the heat upon the objects 12.

The heater 60 may be comprised of various types of heat producing devices or other sanitization devices. Some sanitizing devices include a propane heater, electric heater, natural gas heater, wood heater, hot water heater, radio frequency output device, lexan output device, radiation output device, or solar heat generator. Various other devices may be used as the heater 60 or to sanitize the objects 12 in other manners. Likewise, the present invention includes a fuel supply 61 or power supply generally positioned outside of the chamber 40 (for safety and accessible reasons) to supply the heater 60 with a required fuel. It is appreciated that the heater 60 may be positioned external to the chamber 40 as long as the heated air is directed into the interior of the chamber 40.

The chamber 40 includes one or more, and preferably two, circulation fans 63 mounted above the heater 60 within the directly heated space 51 of the chamber 40. The circulation fans 63 are secured above the heater 60 via a support 64. The circulation fans 63 generally blow directly upon or near the heater 60 and direct the air towards the perforated floor 47 to travel within the passageway 49 towards the indirectly heated space 52 and then rise (through the natural rising process of heated air) onto the object 12. The fans 63 continue to circulate the air within the chamber 40 by pulling air from near the ceiling 45 of the chamber 40 and directing the air towards the perforated floor 47.

The present invention also generally includes a plurality of internal temperature sensors 67 comprised of a probe structure to be inserted within the objects 12 to measure an internal temperature of the objects 12. The sensors 67 are generally comprised of thermistor sensors or thermo couples to measure temperature. The sensors 67 are preferably comprised of a substantially small diameter structure to leave minimal or no marks within the object 12.

Lead wires 68 are connected to the sensors 67 that are directed to one or more controllers 79 within the control room 70 or at another location to allow an operator to monitor the internal temperature of the objects 12 to ensure complete heating of the objects 12 both internally and externally. It is appreciated that the transmission of the data from the sensors 67 to the controller 79 may be accomplished in various manners.

It is also appreciated that the chamber 40 includes one or more ambient or external temperature sensors to record an air temperature external of the objects 12 within the chamber 40. The external temperature sensors (not shown) are generally positioned external to the objects 12 within the interior of the chamber 40, such as within the indirectly heated space 52 to accurately measure the temperature of the ambient air surrounding the object 12. It is appreciated that one or a plurality of external temperature sensors may be used and the external temperatures sensors may use various technologies to measure the ambient temperature.

E. Control Room.

The control room 70 is also generally located upon the frame 21 of the vehicle 20. The control room 70, in the preferred embodiment, is positioned forwardly of the chamber 40, wherein the front wall 42 defines a rear wall of the control room 70. The control room 70 also generally includes sidewalls 71 and a ceiling 75 to completely enclose the control room 70. The sidewalls 71 of the control room 70 and the sidewalls 71 of the chamber 40 are preferably substantially integral as viewed from outside of the vehicle 20. The ceiling 75 is also generally integral with the ceiling 45.

The control room 70 generally includes a door 73 including a handle 74 to access the interior of the control room 70 and one or more windows 72. The control room 70 may also include various vents, electrical outlets, and other mechanics or components to allow for the mechanical and electrical operation of the present invention. The control room 70 also generally includes one or more controllers 79 for recording and viewing temperature data of the chamber 40. The controller 79 may record temperature external and internal to the objects 12, along with heating time, heater 60 statistics, and various other types of data useful in determining the sanitization of the objects 12 within the chamber 40.

The controller 79 or various other transmission devices may also be connected to an external computer (e.g. laptop, etc.) for transferring the heating data thereto. The transferred heat data of the chamber 40 and objects 12 may be compiled and arranged for study of the effectiveness of the heater 60, determination of the sanitization of various parts of the object 12, proof to the customer of internally and externally heating the objects 12 for a specific timeframe 21, and for various other purposes.

F. Operation of Preferred Embodiment.

In use, the object 12 is positioned within the indirectly heated space 52 of the chamber 40. The internal temperature sensors 67 are then inserted within the object 12 at various locations and depths to thoroughly measure the internal temperature of the object 12. The rear door 43 are then closed to seal the chamber 40. The operator then enters the control room 70 and activates the heater 60, the circulation fans 63, and the controller 79.

Heat radiates outward from the heater 60 and the circulation fans 63 direct the heated air 14 to within the passageway 49, under the partition 50, and into the indirectly heated space 52 to contact the object 12 by rising out of the passageway 49. The heated air 14 continues to rise and is pulled towards the circulation fans 63, via the suctioning force of the rotating blades of the circulation fans 63. The heated air 14 continues to circulate throughout the interior of the chamber 40 thus evenly heating the object 12.

Both, the internal temperature of the object 12 and the external temperature of the air surrounding the object 12 are continually monitored via the controller 79 receiving data from the internal temperature sensors 67 and the external temperature sensors. The heater 60 continues to heat the interior of the chamber 40 until both of the internal temperature and the external temperature reaches a predetermined temperature and remains at that predetermined temperature which is known to terminate all insects, bugs, bacteria, etc. Once the desired heat temperature is reached both external and internal to the objects 12, the heater 60 may be turned off and the fans 63 allowed to continue to circulate for a predetermined timeframe 21. The recorded temperature information may be transferred to a data logger as appreciated.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A sanitizer unit for sanitizing objects, comprising:
an enclosed chamber, wherein said enclosed chamber is secured to a mobile trailer;
a heater for heating an interior of said enclosed chamber;
a plurality of internal temperature sensors for measuring an internal temperature of an object positioned within said interior of said chamber;
a plurality of external temperature sensors for measuring an external temperature of air surrounding said object; and
a controller programmed to continually log said internal temperature and said external temperature recorded by said plurality of internal and external temperature sensors, wherein said controller is programmed to turn off said heater after said internal temperature reaches a predetermined internal temperature level and after said external temperature reaches a predetermined external temperature level.

2. The sanitizer unit of claim 1, wherein said enclosed chamber is secured to a vehicle frame.

3. The sanitizer unit of claim 2, including a lift system attached to said vehicle frame for vertically lifting and lowering said vehicle frame.

4. The sanitizer unit of claim 1, wherein said heater is positioned within said interior of said chamber.

5. The sanitizer unit of claim 4, wherein said chamber includes a partition for defining a directly heated space and an indirectly heated space within said interior of said chamber, wherein said heater is positioned within said directly heated space and wherein heat generated from said heater is transferred to said indirectly heated space.

6. The sanitizer unit of claim 5, including at least one circulation fan for transferring said heat from said directly heated space to said indirectly heated space.

7. The sanitizer unit of claim 1, wherein said plurality of internal temperature sensors measuring said internal temperature are comprised of a probe structure.

8. The sanitizer unit of claim 1, wherein said chamber includes a perforated floor and a sub-floor vertically spaced below said perforated floor to define a passageway therebetween, wherein said heated air from said heater is directed through said passageway.

9. A sanitizer unit for sanitizing objects, comprising:
an enclosed chamber having a pair of sidewalls, a front wall, a pair of doors defining a rear wall, wherein said pair of doors allow ingress and egress from an interior of said chamber, a ceiling, a sub-floor, a perforated floor vertically spaced above said sub-floor, and a passageway defined between said sub-floor and said perforated floor, wherein said enclosed chamber is secured to a mobile trailer;
a partition positioned within said enclosed chamber to define a directly heated space and an indirectly heated space within said interior of said chamber, wherein air is able to flow between said directly heated space and said indirectly heated space above and below said partition;
a heater positioned within said directly heated space of said interior of said chamber;
at least one circulation fan suspended above said heater within said directly heated space to direct heated air from said heater within said passageway and towards said indirectly heated space;
a plurality of internal temperature sensors for measuring an internal temperature of an object positioned within said interior of said enclosed chamber;
a plurality of external temperature sensors for measuring an external temperature of air surrounding said object; and
a controller programmed to continually log said internal temperature and said external temperature recorded by said plurality of internal and external temperature sensors, wherein said controller is programmed to turn off said heater after said internal temperature reaches a predetermined internal temperature level and after said external temperature reaches a predetermined external temperature level.

10. The sanitizer unit of claim 9, wherein said enclosed chamber is secured to a vehicle frame.

11. The sanitizer unit of claim 10, including a lift system attached to said vehicle frame for vertically lifting and lowering said vehicle frame.

12. The sanitizer unit of claim 9, wherein said plurality of internal temperature sensors measuring said internal temperature are comprised of a probe structure.

13. The sanitizer unit of claim 9, including a control room extending from said enclosed chamber, wherein said control room is separately accessible with respect to said enclosed chamber.

14. The sanitizer unit of claim 13, wherein said control room and said enclosed chamber are positioned on a vehicle frame.

15. A mattress sanitizer system for eliminating bed bugs, comprising:

- a vehicle frame comprised of a pull-trailer structure;
- wherein said vehicle frame includes a pair of wheels, wherein said pair of wheels are disconnectable from said vehicle frame for lowering and lifting said vehicle frame about said pair of wheels;
- a lift system attached to said vehicle frame for lowering and lifting said vehicle frame, wherein said lift system includes a plurality of actuators;
- an enclosed chamber positioned upon said vehicle frame, said enclosed chamber being adapted to receive a mattress;
- wherein said enclosed chamber is comprised of an insulated structure;
- wherein said enclosed chamber includes a pair of sidewalls, a front wall, a pair of doors defining a rear wall, wherein said pair of doors allow ingress and egress from an interior of said chamber, a ceiling, a sub-floor, a perforated floor vertically spaced above said sub-floor, and a passageway defined between said sub-floor and said perforated floor;
- a partition positioned within said enclosed chamber to define a directly heated space and an indirectly heated space within said interior of said chamber, wherein air is able to flow between said directly heated space and said indirectly heated space above and below said partition;
- a heater positioned within said directly heated space of said interior of said chamber to kill any bed bugs on said mattress;
- at least one circulation fan suspended above said heater within said directly heated space to direct heated air from said heater within said passageway and towards said indirectly heated space;
- at least one object positioned within said indirectly heated space to be sanitized with heated air from said heater;
- a plurality of internal temperature sensors comprised of a probe structure to be inserted within said at least one object towards a core of said at least one object for determining an internal temperature of at least one object;
- at least one external temperature sensor positioned within an interior of said chamber for measuring an ambient temperature within said interior of said chamber;
- a control room positioned upon said vehicle frame, wherein said control room is separately accessible than said enclosed chamber; and
- a controller positioned within said control room, wherein said controller is programmed to control said heater and said at least one circulation room;
- wherein said controller is connected to said plurality of internal temperature sensors and said at least one external temperature sensor, said controller being programmed to receive recorded temperatures of said plurality of internal temperature sensors and said at least one external temperature sensor, wherein said controller is programmed to turn off said heater after said internal temperature reaches a predetermined internal temperature level and after said ambient temperature reaches a predetermined external temperature level.

\* \* \* \* \*